United States Patent
Pearce

(10) Patent No.: US 6,723,057 B1
(45) Date of Patent: Apr. 20, 2004

(54) CELL SAMPLING SPATULA

(75) Inventor: Harold James Pearce, Tetbury (GB)

(73) Assignee: Platinum Feather Consultants Limited, Gloucestershire (GB)

( * ) Notice: Subject to any disclaimer, the term of this patent is extended or adjusted under 35 U.S.C. 154(b) by 0 days.

(21) Appl. No.: 09/826,379

(22) Filed: Apr. 4, 2001

(30) Foreign Application Priority Data

Feb. 6, 2001 (GB) .............................................. 0102952

(51) Int. Cl.[7] .............................................. A61B 10/00
(52) U.S. Cl. ........................ 600/570; 600/562; 606/160
(58) Field of Search .............................. 600/562, 569, 600/570, 571, 572; 606/160; 604/1; 435/40.5; 294/57, 59

(56) References Cited

U.S. PATENT DOCUMENTS

| | | | | |
|---|---|---|---|---|
| 3,774,590 A | * | 11/1973 | McDonald | .................. 600/570 |
| 3,815,580 A | * | 6/1974 | Oster | ......................... 600/572 |
| 3,961,620 A | * | 6/1976 | Schack et al. | ............... 600/570 |
| 4,620,548 A | * | 11/1986 | Hasselbrack | ................. 600/571 |
| 4,981,143 A | * | 1/1991 | Sakita et al. | ................. 600/570 |
| 5,623,941 A | * | 4/1997 | Hedberg et al. | ............ 600/569 |
| 6,291,234 B1 | * | 9/2001 | Raz et al. | ................. 435/309.1 |

\* cited by examiner

*Primary Examiner*—Charles Marmor
(74) *Attorney, Agent, or Firm*—Nath & Associates PLLC; Harold L. Novick

(57) ABSTRACT

A spatula for taking cell samples for histological examination formed with a body portion and a head portion, in which the spatula is formed from a non-absorbent plastics material and includes a frangible zone between the body and the neck portions whereby the head portion can be broken away from the body portion by relative bending about a lateral axis in the frangible zone. The frangible zone preferably has sufficient strength to resist fracture under rotational forces about the longitudinal axis of the spatula during use.

10 Claims, 1 Drawing Sheet

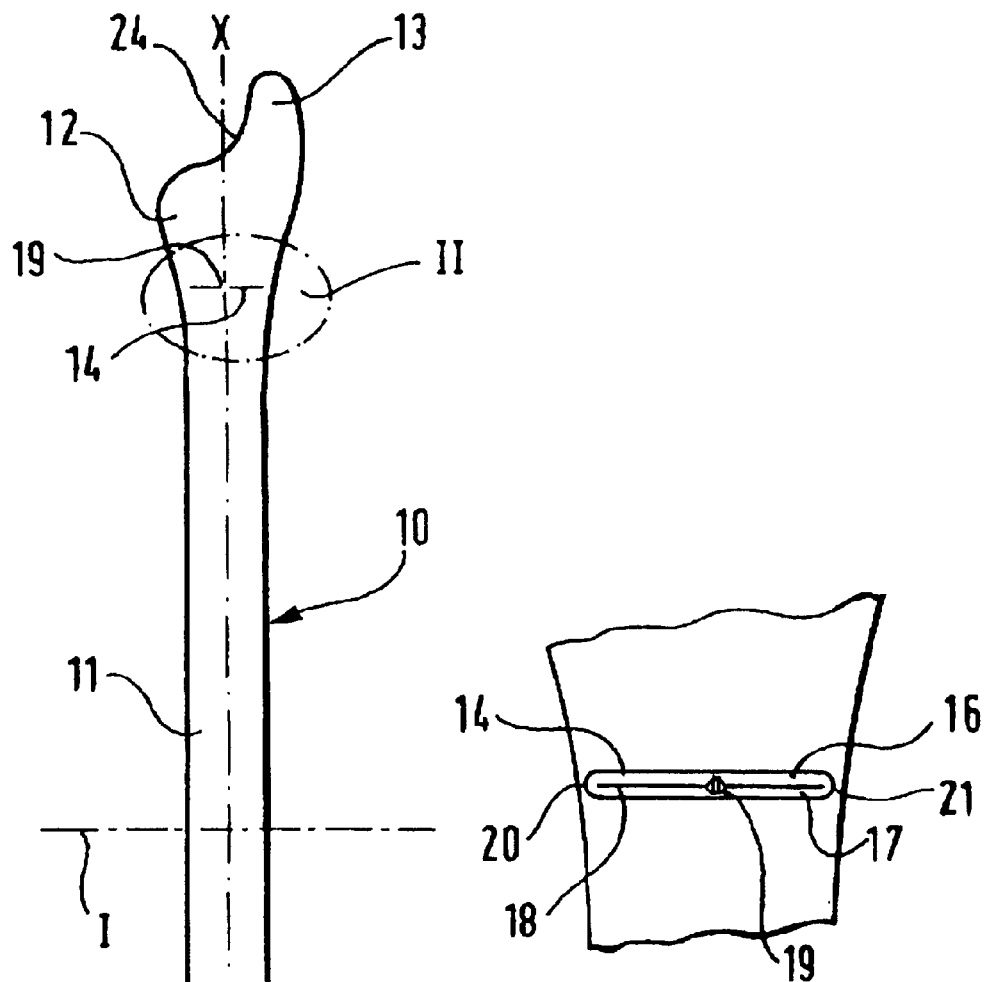
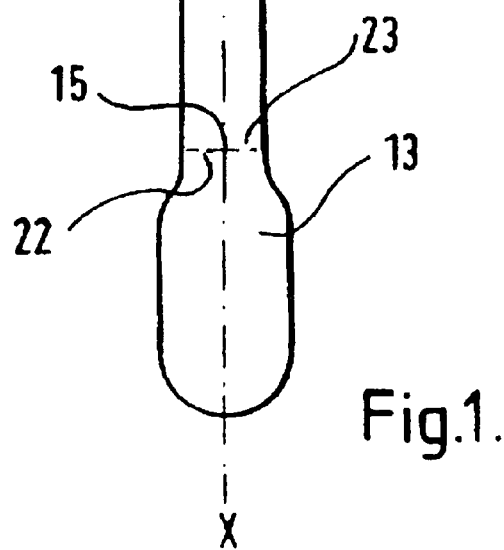
Fig.2.
Fig.1.

CELL SAMPLING SPATULA

TECHNICAL FIELD

This invention relates to spatulas for taking cell samples from the body for histological examination, especially for use in taking samples for analysis in screening for cervical cancer.

BACKGROUND OF THE INVENTION

Spatulas for gynecological cytology and cervical cancer screening are conventionally made from wood and typically comprise an elongate body portion and a head portion shaped that includes a side lobe. Spatulas having this type of construction are often referred to by those with skill in the art as "Aylesbury Spatulas." The spatula is used to sample cells at the transformation zone, which may be invisible to the naked eye, between the columnar and squamous epithelium of the uterine cervix, which is also commonly referred to as the squamo-columnar junction, where precancerous changes are most likely to occur. Where the transformation zone is visible, the spatula can be rotated through 360 degrees around the cervix, to sample the transformation zone. Where the transformation zone is within the cervical canal, the endocervix may be similarly sampled so as to maximize the collection of a useful cell sample.

In use, more specifically, the spatula is inserted in the vagina so that the head portion contacts the cervix and the body portion is then rotated about its longitudinal axis so that an inner edge of the side lobe of the head portion scrapes around the exterior wall of the cervix, removing therefrom a sample of cells. Conventionally, the sample is then transferred to a glass slide to provide a "smear" for histological examination by microscope. However such examination is necessarily subjective and therefore potentially unreliable and, indeed, the technique has occasionally given rise to publicly expressed concerns regarding the effectiveness of screening programs in some hospitals. In any event, the act of transferring the sample to the slide involves subjecting the sample to shearing forces, which can physically damage or distort the cells, making interpretation of results more difficult.

In an attempt to avoid the problems of manual analysis, apparatus for automated examination by so-called liquid base cytology has more recently been developed. In use, the sample from the spatula is added to a liquid to form a suspension of cells and it has been found that the results of the ensuing examination are far more consistently reliable than with manual examination. However, a disadvantage is that the wooden spatula tends to absorb the liquid, resulting in difficulty in obtaining complete transfer of the sample to the liquid and a consequential weak or dilute liquid-base sample for cytological analysis.

Accordingly, what has been needed but heretofore unavailable is a spatula of the type described that can be used for obtaining samples both for manual and automated analysis but which especially overcomes the problems of wooden spatulas when the samples are analyzed by liquid base cytology and which reduces or eliminates the likelihood of damage to the sample.

The present invention meets these and other needs without adding any complexity, inefficiencies, or significant costs to procurement and use of cell sampling spatulas. The various embodiments, modifications, and variations of the present invention disclosed herein are readily adapted for ease of manufacture, low fabrication costs, and immediate compatibility with both the cell sampling and examination techniques presently in use and prospective techniques not yet developed or established.

SUMMARY OF INVENTION

In its most general sense the present invention overcomes the shortcomings of the prior art in any of a number of generally effective configurations. According to one aspect of the present invention, a spatula for taking cell samples for histological examination includes a body portion and a head portion, in which the spatula is formed from a non-absorbent plastics material and includes a frangible zone between the body and neck portions whereby the head portion can be broken away from the body portion by relative bending about a lateral axis in the frangible zone, the frangible zone nevertheless having sufficient strength to resist fracture under rotational forces about the longitudinal axis of the spatula in use. Preferably, the plastic material may be sterilized for applications requiring a contamination free examination environment.

The surface of the spatula, which is conventionally of a generally flat configuration, or at least of the head portion thereof, and preferably is formed to have a surface texture that is adapted to capture and retain sample cells. The surface texture may include, for example without limitation, stippled, dimpled, satin-effect, or roughened surfaces, or any combination thereof.

The frangible zone may comprise any structural feature which provides a weakness in terms of relative bending resistance between the head and body portions about a lateral axis in the frangible zone while not significantly compromising the rotational strength as between the head and body portions under twisting forces about the longitudinal axis of the spatula. The frangible zone may comprise a lateral groove or channel between the head and body portions on one or preferably both sides of the spatula.

Preferably, the channel or each groove is closed-ended in that it does not extend to the edges of the spatula and optionally the groove is provided with one or more intermediately-located fillets or webs to moderate the weakness. Where a groove is formed on each side of the spatula, they preferably coincide on respective sides whereby the lateral axis of weakness passes through the bridging material forming a common base to and extending between the respective grooves. The fillets are preferably alternately disposed in such respective grooves.

A suitable plastics material for formation of spatulas according to the invention is preferably a thermoplastic material that can include, for example, acetal resins, delrin, fluorocarbons, polyesters, polyester elastomers, polyolefins, metallocenes, polyamides, nylon, polyvinyl chloride, polybutadienes, silicone resins, acrylontrile-butadiene-styrene plastics (ABS), polypropylene, liquid crystal polymers, combinations ard mixtures and composites thereof, and reinforced combinations and mixtures and composites thereof.

For functional and economic reasons, the thickness of the spatulas should be preferably within the range of about 1.0 mm to 4.0 mm (millimeters), and more preferably between about 1.5 mm and 2.5 mm, and more preferably about 2.0 mm. The groove or grooves should extend in depth to approximately two thirds of the thickness in aggregate, especially where they are coincident on respective sides. Should the grooves be included only on a single side or be disposed in an offset relationship, their aggregate depth could be greater, for example up to 1.5 times the thickness of the material.

Spatulas according to the invention may also have an enlarged tail portion remote from the head portion, shaped for example as an oval, and such tail portion may likewise be formed with a frangible zone and be adapted for uses similar to that of the head portion.

These variations, modifications, and alterations of the various preferred embodiments may be used either alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures, wherein like reference numerals across the several drawings refer to identical, corresponding, or equivalent elements, features, and parts:

FIG. 1 is top, planform view, in reduced scale, of a spatula according to the present invention showing the front side of the head portion end of the spatula, and the rear side of the tail portion end; and FIG. 2 is a view, in enlarged scale, of the apparatus of FIG. 1 taken about the region encircled with detail view line 2—2.

DESCRIPTION OF THE PREFERRED EMBODIMENT

The cell sampling spatula of the instant invention is a significant advance in the state of the art of such articles in that is compatible with well-established sampling techniques as well as relatively recent sampling and examination methods. The preferred embodiments and described and contemplated modifications of the spatula accomplish this by new and novel configurations and arrangements of elements that are configured in unique and unobvious ways and which demonstrate previously unavailable capabilities.

With reference now to the accompanying figures and specifically to FIGS. 1 and 2, a spatula, shown generally by reference numeral 100, is formed from a flat strip of a non-absorbent thermoplastic plastics material having a slightly textured surface that may incorporate stippled, dimpled, satin-effect, and roughened surfaces, and combinations thereof. The body of the spatula has a thickness of preferably between about 1.0 mm–4.0 mm, and more preferably between approximately 1.5 mm and 2.5 mm, and even more preferably about 2.0 mm. The spatula 100 consists of a body portion 110, and a head portion 120 and tail portion 135. For convenience in illustration, a front side of the head portion 120 and the upper part of the body portion is shown above the line denoted by reference roman numeral I, whereas the rear side of the tail portion 135 and the lower part of the body portion is shown below the line I, as though the bottom portion of spatula 100 had been rotated about the axis of rotation formed by the center line denoted generally by reference letters X—X.

The head portion 120 has a generally flared profile with an axially-extending lobe 130. The neck between the head and body portions is formed with at least one weakened region that forms a frangible portion, which is shown for illustration purposes as a V-shaped groove 140, as described later with reference to and as shown in more detail in FIG. 2. The tail portion 135 of the spatula 100 is formed with an oval profile and also has at least one weakened region that forms a frangible portion, which can be a V-shaped groove 150.

Although a groove having a generally V-shaped cross-sectional profile is shown and described, any of an equally suitable number of similar cross-sections may also be incorporated, including, for example, a slot, a channel, or other similar depression that can have any type of equally effective rectilinear or curvilinear cross-sectional profile.

Referring also now to FIG. 2, the sides 160, 170 of the groove 140 slope inwardly to the bottom 180 and the groove is bridged centrally by at least one fillet 190 which extends almost to the front surface 145 of the spatula 100. The groove 140 terminates inwardly of the edges of the spatula 100 in end walls 200, 210 and thus is closed-ended.

Referring back again specifically to FIG. 1, the groove 150 is similar in formation to the groove 140 but has one or more fillets, webs, stiffeners, ribs, bridge elements, and spanners, such as, for example without limitation, fillets 220, 230. In variations of this embodiment, a groove similar to groove 150 is also formed in the rear face of the spatula 100 (not shown), immediately behind groove 140, and a groove similar to groove 140 is also formed in the rear face of the spatula 100, immediately behind groove 150, whereby the fillets in each pair of grooves may be or are in alternating disposition. In other variations, the fillets may be aligned, such as in the case where the groove is replaced with a slotted arrangement. In further variations of the arrangement, each groove is preferably approximately one third the thickness of the spatula 100 in depth and the material of the spatula 100 between the bottoms of each respective back-to-back pair of grooves constitutes a frangible zone or region of weakness.

In use, the head portion 120 of the spatula 100 is inserted in the vagina, and the inner edge 240 of the lobe 130 is positioned to contact the cervix. The spatula 100 is then rotated about its longitudinal axis X—X to encircle the cervix and to capture a sample of cells for removal and examination. The sample adheres to the surface of head portion 120 of the spatula 100 proximate to the edge 240.

The sample cells may then be smeared on an analysis medium such as a glass slide (not shown) for conventional examination, or for liquid base cytology, they may be transferred to a container of a liquid analysis medium (not shown). For the latter application, the entire head portion 120 of the spatula 100 is immersed in the liquid and, with the tip of the lobe 130 in contact with the base of the container, a downwards and sideways force is exerted on the body portion 110 so that the head portion 120 bends relative to the body portion 110 about the lateral axis which coincides with the zone of weakness between the bottoms of the groove 140 and the corresponding groove formed in the rear face. The head portion 120 may break off entirely from the body portion 110 on being thus bent in one direction. More preferably, the frangible zone has sufficient strength, by virtue of the fillets in the grooves and the end walls of the grooves, or similarly capable weakened region configurations, to require bending in the other direction before complete fracture takes place. By selecting a material, a thickness, and a fillet configuration or some combination thereof, selected for adequate resilience and strength, the head portion 120 will preferably not break off under rotation force when in the vagina. Instead, it will fracture cleanly on application of bending forces first in one direction and then in the other when the spatula is placed in the liquid analysis medium container. In this way, the entire cell sample is transferred to the test liquid without physical damage to the cells in the sample. In other various cell sampling applications, those with skill in the art will understand that the tail portion 135 may be used in a manner similar to that described with reference to head portion 120.

In modifications to any of the preceding embodiments, the grooves described above may be replaced with partial or through slots (not shown), in spatula 100 configurations having sufficient thickness. The slots may further incorporate frangible side-walls and/or frangible webs, stiffeners, ribs, bridge elements, and spanners sized and positioned to span the slot to impart adequate strength during use while enabling controlled separation upon application or the aforementioned bending forces.

Numerous alternatives, alterations, modifications, and variations of the preferred embodiments disclosed herein will be apparent to those skilled in the art and they are all contemplated to be within the spirit and scope of the instant invention. For example, although specific embodiments have been described in detail, those with skill in the art will understand that the preceding embodiments and variations can be modified to incorporate various types of substitute and/or additional materials, relative arrangement of elements, and dimensional configurations for compatibility with the wide variety of cellular and tissue sampling techniques, methods, and applications. Accordingly, even though only few embodiments, modifications, alternatives, and variations of the present invention are described herein, it is to be understood that the practice of such additional modifications and variations and the equivalents thereof, are within the spirit and scope of the invention as defined in the following claims.

I claim:

1. A spatula for taking cell samples for histological examination, comprising:
   a body portion formed with a head portion connected to the body portion by a frangible zone;
   wherein the spatula is formed from a non-absorbent polymeric material;
   wherein the frangible zone incorporates at least one weakened region that includes an element selected from the group including a groove, a channel, a recess, a slot, a depression having a rectilinear cross-sectional profile, and a depression having a curvilinear cross-sectional profile; and
   at least one frangible strengthener formed to span the at least one weakened region, the strengthener selected from the group including fillets, webs, stiffeners, ribs, bridge elements, and spanners.

2. The spatula according to claim 1, wherein the at least one frangible strengthener is disposed in the weakened region on one side of the spatula to be superimposed on another at least one strengthener on the opposite side.

3. The spatula according to claim 1, wherein the at least one frangible strengthener is disposed in the weakened region on one side of the spatula to not be superimposed on another at least one strengthener on the opposite side.

4. A spatula for taking cell samples for histological examination, comprising:
   a body portion formed with a head portion connected to the body portion by a frangible zone;
   wherein the spatula is formed from a non-absorbent polymeric material;
   wherein the frangible zone incorporates at least one weakened region that includes an element selected from the group including a groove, a channel, a recess, a slot, a depression having a rectilinear cross-sectional profile, and a depression having a curvilinear cross-sectional profile, and
   wherein the weakened region is closed-ended.

5. A spatula for taking cell samples for histological examination, comprising:
   a body portion formed with a head portion and an opposite tail portion, the head and tail portions being each connected to the body portion by at least one respective head and tail frangible zone;
   wherein the spatula is formed from a non-absorbent polymeric material;
   wherein the frangible zone incorporates at least one weakened region that includes an element selected from the group including a groove, a channel, a recess, a slot, a depression having a rectilinear cross-sectional profile, and a depression having a curvilinear cross-sectional profile; and
   at least one frangible strengthener formed to span the at least one weakened region, the strengthener selected from the group including fillets, webs, stiffeners, ribs, bridge elements, and spanners.

6. The spatula according to claim 5, wherein the at least one frangible strengthener is disposed in the weakened region on one side of the spatula to be superimposed on another at least one strengthener on the opposite side.

7. The spatula according to claim 5, wherein the at least one frangible strengthener is disposed in the weakened region on one side of the spatula to not be superimposed on another at least one strengthener on the opposite side.

8. A method for taking cell samples for histological examination, that includes the steps of:
   selecting a spatula formed from a non-absorbent polymeric material and having a body portion formed with a head portion connected to the body portion by a frangible zone incorporating at least one weakened region that includes an element selected from the group including a groove, a channel, a recess, a slot, a depression having a rectilinear cross-sectional profile, and a depression having a curvilinear cross-sectional profile, the frangible zone further including at least one frangible strengthener formed to span the at least one weakened region, the strengthener selected from the group including fillets, webs, stiffeners, ribs, bridge elements, and spanners;
   collecting a cell sample by scraping the spatula against a source tissue surface to retain the sample cells on the spatula; and
   introducing the cell sample to an analysis medium.

9. The method according to claim 8, wherein the analysis medium is a slide and the introducing step further includes the step of introducing the cell sample to the slide by smearing.

10. The method according to claim 8, wherein the analysis medium is a cytological liquid and the introducing step further includes the step of inserting the portion of the spatula having the cell sample into the liquid, applying a bending force and motion to the spatula to fracture the spatula about the frangible zone, removing the remaining portion of the spatula and leaving the detached portion of the spatula in the liquid.

* * * * *